US010943700B2

(12) United States Patent
Kim

(10) Patent No.: US 10,943,700 B2
(45) Date of Patent: Mar. 9, 2021

(54) METHOD FOR APPARATUS, SERVER AND METHOD OF PROVIDING SELF-DIAGNOSIS RESULT AND MEDICAL INFORMATION

(71) Applicant: Soo Koun Kim, Changwon-si Gyeongsangnam-do (KR)

(72) Inventor: Soo Koun Kim, Changwon-si Gyeongsangnam-do (KR)

( * ) Notice: Subject to any disclaimer, the term of this patent is extended or adjusted under 35 U.S.C. 154(b) by 233 days.

(21) Appl. No.: 15/881,927

(22) Filed: Jan. 29, 2018

(65) Prior Publication Data

US 2019/0237193 A1    Aug. 1, 2019

(51) Int. Cl.
| | |
|---|---|
| *G16H 50/30* | (2018.01) |
| *G16H 10/60* | (2018.01) |
| *G16H 30/40* | (2018.01) |
| *G16H 50/70* | (2018.01) |
| *G06F 16/951* | (2019.01) |

(52) U.S. Cl.
CPC .......... *G16H 50/30* (2018.01); *G06F 16/951* (2019.01); *G16H 10/60* (2018.01); *G16H 30/40* (2018.01); *G16H 50/70* (2018.01)

(58) Field of Classification Search
CPC ........ G16H 50/30; G16H 10/60; G16H 50/70; G16H 30/40; G06F 16/951
USPC .............................................................. 705/3
See application file for complete search history.

(56) References Cited

U.S. PATENT DOCUMENTS

2015/0227708 A1* 8/2015 Jung ...................... G06Q 10/06
705/2

FOREIGN PATENT DOCUMENTS

| CN | 103454515 A | * | 12/2013 | ............ G01R 31/00 |
| JP | 2005071092 A | * | 3/2005 | ............ G06F 17/60 |
| KR | 20020077671 A | * | 10/2002 | ............... G06N 5/04 |
| RU | 2286711 C2 | * | 11/2006 | ............ G16H 50/20 |
| WO | WO-2016183904 A1 | * | 11/2016 | ............ G16Z 99/00 |

OTHER PUBLICATIONS

Jutel, A. & Lupton, D. (2015). Digitizing diagnosis: a review of mobile applications in the diagnostic process. Diagnosis, 2(2), pp. 89-96. Retrieved Jan. 7, 2020, from doi:10.1515/dx-2014-0068 (Year: 2015).*
Baray, J., & Cliquet, G. (2013). Optimizing locations through a maximum covering/p-median hierarchical model: Maternity hospitals in France. Journal of Business Research, 66(1), 127-132. (Year: 2013).*

* cited by examiner

*Primary Examiner* — Janice A Mooneyham
*Assistant Examiner* — Winston Furtado
(74) *Attorney, Agent, or Firm* — Dinsmore & Shohl LLP; Yongsok Choi, Esq.

(57) ABSTRACT

The present disclosure includes an input module, a memory in which a self-diagnostic application is stored, and a processor configured to execute the self-diagnostic application. Herein, upon execution of the self-diagnostic application, the processor extracts multiple queries corresponding to a body part selected by a user on the basis of the user's input signal to select any one of multiple body parts and generates a diagnosis result for the user on the basis of the user's answers to the multiple queries. Further, the diagnosis result corresponds to at least one of multiple diseases.

8 Claims, 7 Drawing Sheets

METHOD FOR APPARATUS, SERVER AND METHOD OF PROVIDING SELF-DIAGNOSIS RESULT AND MEDICAL INFORMATION

TECHNICAL FIELD

The present disclosure relates to a diagnostic apparatus, a server that provides medical information, and a method of providing a self-diagnosis result of the diagnostic apparatus.

BACKGROUND

With the recent proliferation of smartphones, the number of applications that provide medical information has increased.

A medical information providing application shows the surrounding hospitals or pharmacies on the basis of location information. Further, the medical information providing application may show hospitals or pharmacies by specialty subjects, themes, or symptoms. For example, the specialty subjects may include dentistry, pediatry, otolaryngology, and ophthalmology. Also, the themes may include various kinds of clinics or hospitals for night care, and the symptoms may include chronic fatigue, atopy, and obesity.

When a user selects a specialty subject or a symptom, the medical information providing application displays information about hospitals corresponding thereto. For example, the medical information providing application may display information about a hospital such as office hours and specialty subjects of the hospital. Further, the medical information providing application may be combined with a map application programming interface (API) to display the surrounding hospitals on a map image.

SUMMARY

In view of the foregoing, the present disclosure provides a diagnostic apparatus capable of providing a self-diagnosis result on the basis of a user's answers to queries, a server that provides medical information, and a method of providing a self-diagnosis result of the diagnostic apparatus.

However, problems to be solved by the present disclosure are not limited to the above-described problems. There may be other problems to be solved by the present disclosure.

According to a first aspect of the present disclosure, a diagnostic apparatus configured to provide a self-diagnosis result includes an input module, a memory in which a self-diagnostic application is stored, and a processor configured to execute the self-diagnostic application. Herein, upon execution of the self-diagnostic application, the processor extracts multiple queries corresponding to a body part selected by a user on the basis of the user's input signal to select any one of multiple body parts and generates a diagnosis result for the user on the basis of the user's answers to the multiple queries. Further, the diagnosis result corresponds to at least one of multiple diseases.

According to a second aspect of the present disclosure, a medical information providing server includes a communication module, a memory in which a diagnosis result providing program is stored, and a processor configured to execute the program. Herein, upon execution of the program, the processor transfers a diagnosis result received from a user device to a medical team device. The diagnosis result is generated through the user device on the basis of answers to multiple queries and corresponds to at least one of multiple diseases.

Further, according to a third aspect of the present disclosure, a method of providing a self-diagnosis result to be performed by a diagnostic apparatus includes: extracting multiple queries corresponding to a body part selected by a user on the basis of the user's input signal to select any one of multiple body parts; and generating a diagnosis result for the user on the basis of the user's answers to the multiple queries. Herein, the queries correspond to at least one of multiple diseases.

According to the present disclosure, it is possible to generate a diagnosis result including a user's disease by analyzing the user's answers to queries and then provide the diagnosis result to the user. Therefore, the present disclosure enables the user to select a hospital on the basis of the diagnosis result matched to his/her symptom and take medical treatment.

According to the present disclosure, it is possible to provide a medical team with a diagnosis result as preliminary medical examination information. Further, according to the present disclosure, it is possible to provide the medical team with data including the user's diagnosis result and past medical records. Therefore, the present disclosure can support the medical team to make a diagnosis with high accuracy and high efficiency on the basis of the data.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
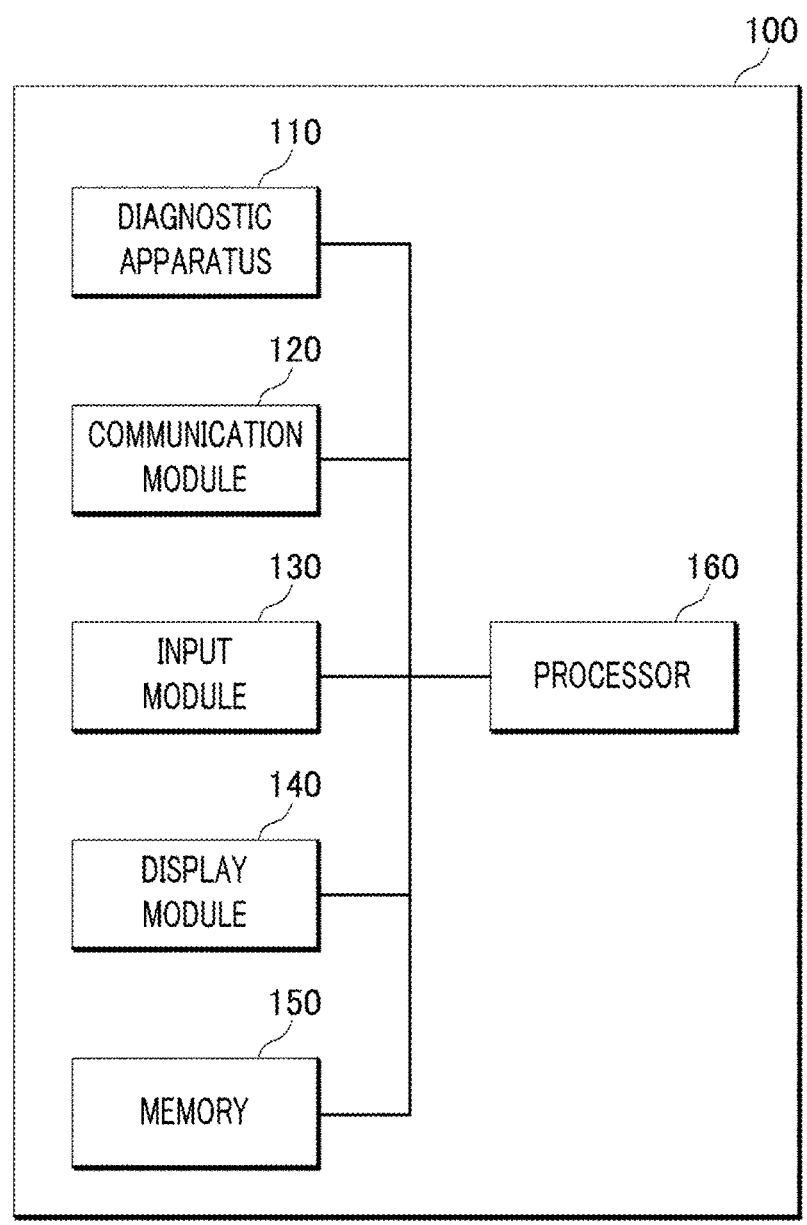
FIG. 1 is a block diagram illustrating a diagnostic apparatus according to an exemplary embodiment of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Hereinafter, a diagnostic apparatus 100 according to an exemplary embodiment of the present disclosure will be described with reference to FIG. 1 to FIG. 3.

FIG. 1 is a block diagram illustrating the diagnostic apparatus 100 according to an exemplary embodiment of the present disclosure.

The diagnostic apparatus 100 refers to a user side apparatus, and provides a self-diagnosis result corresponding to a user's symptom at the request of the user. Herein, the diagnostic apparatus 100 may be a mobile device such as a smartphone or a computing device such as a PC and a notebook computer, but may not be limited thereto.

The diagnostic apparatus 100 includes a communication module 110, an input module 130, a display module 140, a memory 150, and a processor 160.

The communication module 110 may perform data communication with a medical information providing server 410 that provides medical information or information about hospitals.

The input module 130 receives the user's interaction. In this case, if a user device is a smart device, the input module 130 may be a resistive or capacitive touch screen panel and may be implemented as integrated with the display module 140. For example, if the input module 130 is a touch panel that supports a multi-touch operation, the device user may input an interaction sing his/her finger or a tool such as a touch pen. Further, the input module 130 may be an input device such as a keyboard, a mouse, a joystick, and a touch pad.

The display module 140 may display a user interface for self-diagnosis.

The memory 150 stores a self-diagnosis application therein. Herein, the memory 150 may collectively refer to a non-volatile storage device that retains information stored therein even when power is not supplied and a volatile storage device that requires power to retain information stored therein.

The diagnostic apparatus 100 may further include a GPS (global positioning system) sensor module 120 for detecting location information or a sensor module capable of extracting location information.

The processor 160 may provide disease information classified by disease in order to enable the user to find the disease information. In this case, the disease information may include the name of the disease, major symptoms, and information about hospitals matched to the disease.

Further, the processor 160 may enable the user to obtain a diagnosis result for his/her symptom by answering simple queries provided through the self-diagnosis application. In this case, the processor 160 may provide the queries to the user and receive the user's answers through the self-diagnosis user interface included in the self-diagnosis application. Herein, the self-diagnosis user interface will be described in detail with reference to FIGS. 2A through 2C.

Figure 2A:
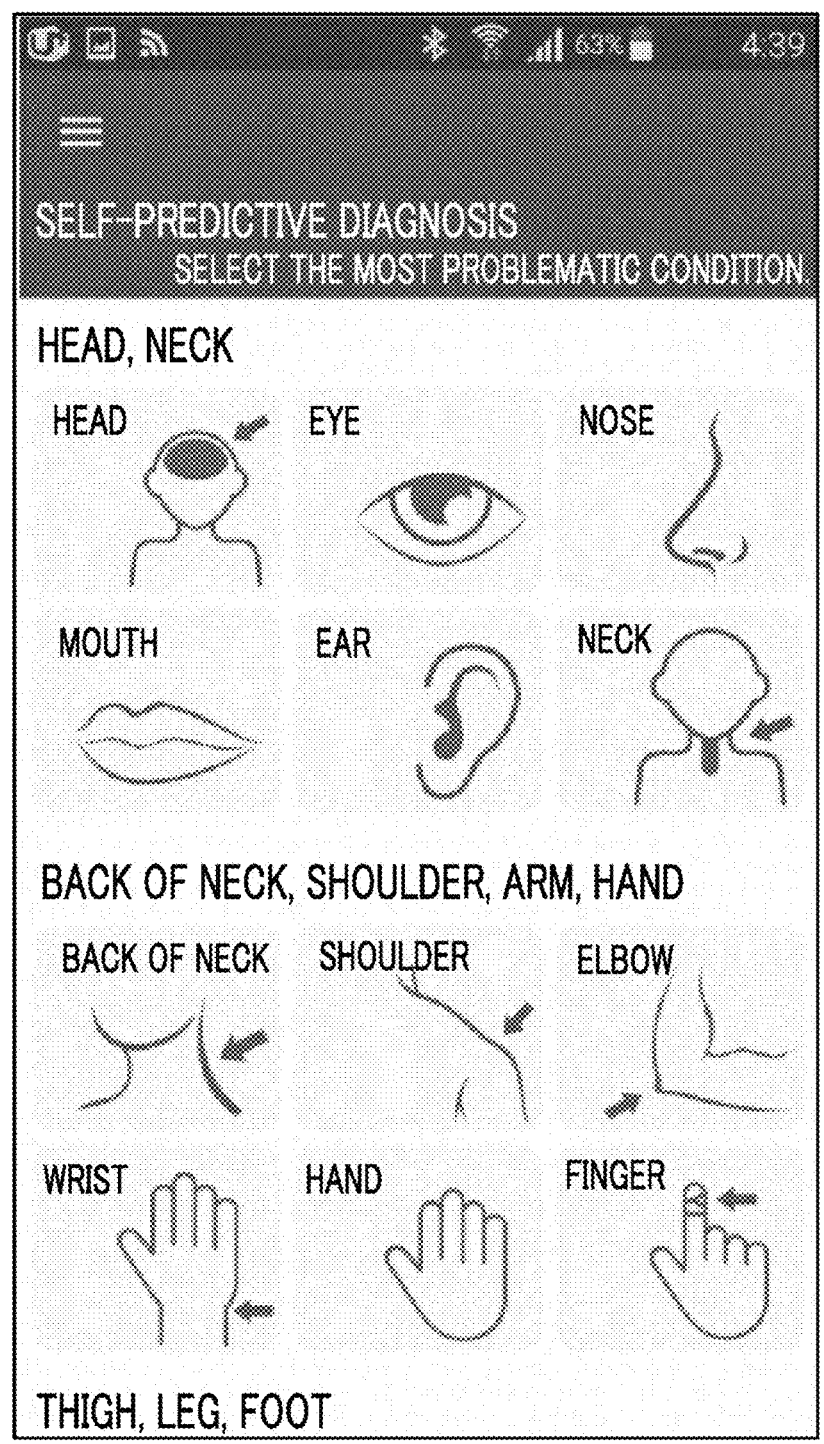
FIGS. 2A to 2C are exemplary diagrams illustrating a self-diagnosis user interface according to an exemplary embodiment of the present disclosure.
Figure 2B:
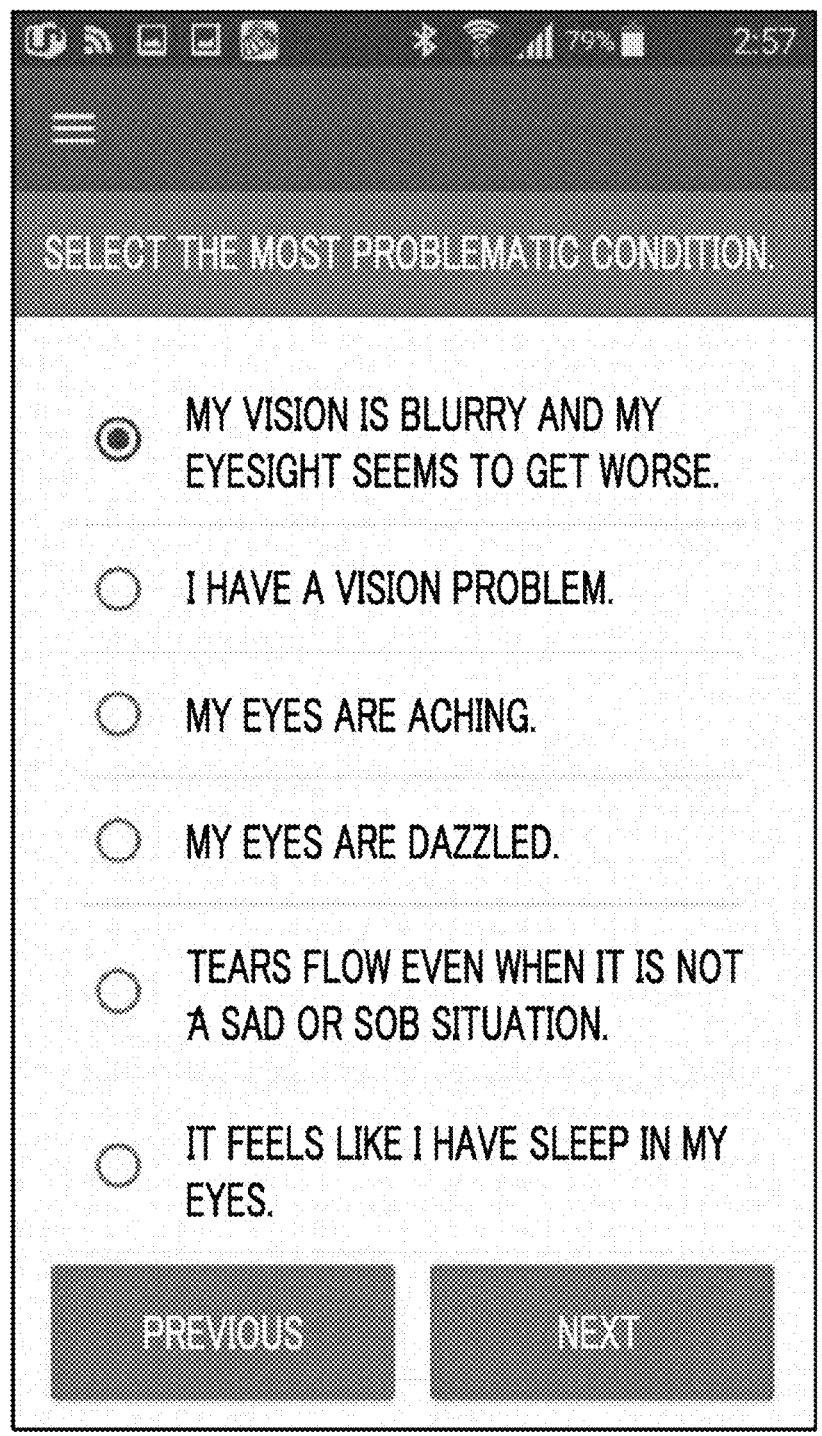
Figure 2C:
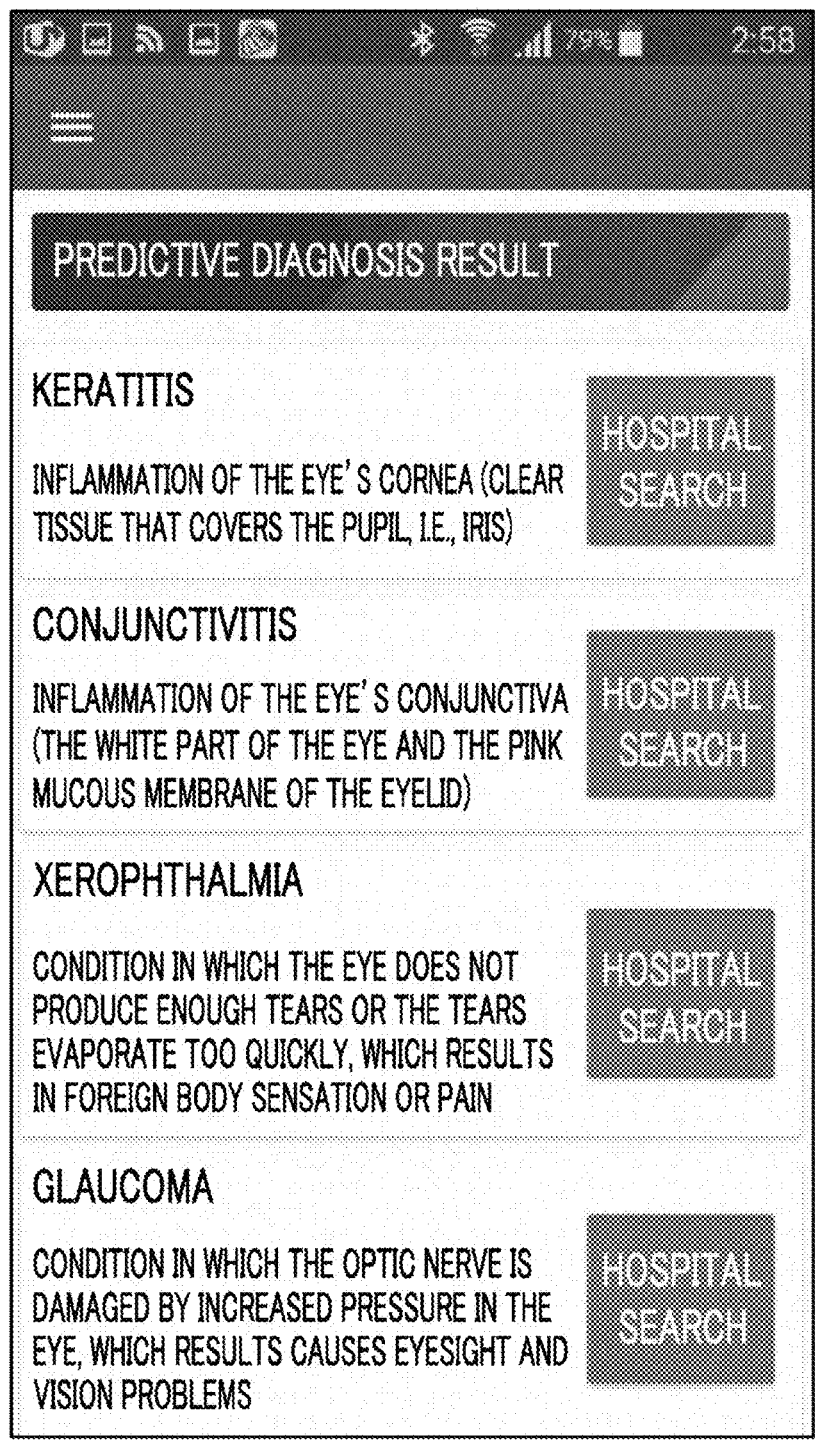

FIGS. 2A through 2C are exemplary diagrams illustrating a self-diagnosis user interface according to an exemplary embodiment of the present disclosure.

Referring to FIG. 2A, the self-diagnosis user interface may include images corresponding to multiple body parts. In this case, the body parts refer to a human body divided into parts. For example, the body parts may include head, eye, nose, mouth, ear, neck, hand, leg, foot, and shoulder. Otherwise, in the case of diseases such as skin diseases which cannot be classified just by a specific body part, information such as a photo or name representing a disease may be provided for user selection.

The user may select a body part corresponding to his/her symptom from among the multiple body parts through the input module 130.

The processor 160 may display multiple queries corresponding to the body part selected according to the user's input signal on the display module 140. In this case, the multiple queries may be stored in the memory 150 or a storage module. Otherwise, the multiple queries may be stored in the medical information providing server 410 and may be received through the communication module 110.

In this case, each query may be matched to a select button or an answer button in order for the user to select a query when the query corresponds to his/her symptom. Further, each query may include an input window in order for the user to input a short answer.

For example, referring to FIG. 2B, the processor 160 may match multiple queries to select buttons for the respective queries and display them on the display module 140 through the self-diagnosis interface in order for the user to select a query corresponding to his/her symptom.

The user may select one or more queries corresponding to his/her symptom from among the multiple queries through the input module 130. The processor 160 may analyze answers corresponding to the queries selected by the user. In this case, the processor 160 may analyze the answers selected by the user on the basis of predetermined weightings.

A weighting may be set for a query matched to a specific disease. Further, a weighting included in a specific query may be differently set for each disease.

TABLE 1

|  | Answer to first query | Answer to second query | Answer to third query | Answer to fourth query | Answer to fifth query |
|---|---|---|---|---|---|
| First disease | 1 | 0 | 0 | 1 | 0 |
| Second disease | 0 | 2 | 3 | 0 | 1 |
| Third disease | 0 | 1 | 1 | 0 | 1 |

For example, weightings for answers to respective queries corresponding to three diseases may be set as shown in Table 1. Referring to the drawings, if an answer "My vision is blurry and my eyesight seems to get worse" is selected for a first query "Select the most problematic condition", diabetic retinopathy (first disease) may be given a weighting of 1 and xanthosis (second disease) and cataract (third disease) may be given a weighting of 0. Further, if an answer "My view is obscured" is selected for a second query "Is your view clear?", diabetic retinopathy (first disease), xanthosis (second disease), and cataract (third disease) may be given weightings of 0, 2, and 1, respectively. That is, a weighting may vary depending on the degree of association between an answer and a disease. As such, weightings for respective diseases with respect to all of answers can be calculated.

In this case, there is no association between an answer and a disease, the disease may be given a weighting of 0. That is, the answers to the first query and the fourth query correspond to the first disease only. Further, the answers to the second query, the third query, and the fifth query correspond to the second disease and the third disease.

Herein, as an additional exemplary embodiment, in the case where a symptom included in the answers is the same as that of various diseases, each disease is given a weighting and may be given a different weighting depending on whether the symptom is highly likely to appear in the disease or whether the symptom is a major symptom of the disease. Further, the formation of queries may change organically depending on the user's answer. For example, if a score for a disease associated with a symptom of loss of vision with respect to first five queries is different by a predetermined score from that of another disease, queries corresponding to diseases associated with the symptom of loss of vision may be subsequently selected and provided. Specifically, for example, if multiple categories of regional symptoms are set and a score for a disease in a specific category is high, queries to be provided subsequent to some queries may be associated with the disease in the specific category.

As for an answer to the second query, the second disease may be given a weighting of 2 and the third disease may be given a weighting of 1. That is, as for an answer to the second query, two diseases may be given different weightings, respectively. Further, as for an answer to the fifth query, the second disease and the third disease may be given a weighing of 1. That is, as for an answer to the fifth query, two diseases may be given the same weighing.

The processor 160 may calculate the sum of weightings for each disease according to the queries selected by the user as a score for each disease. That is, a score for the first disease may be 2, a score for the second disease may be 6, and a score for the third disease may be 3.

The processor 160 may select a predetermined number of diseases in order of score. Further, the processor 160 may generate a diagnosis result including the selected diseases and information about the diseases. The processor 160 may display the generated diagnosis result on the display module 140.

For example, if the predetermined number is 1, the processor 160 may select the second disease with the highest score as a disease corresponding to the user. Then, the processor 160 may display a diagnosis result corresponding to the selected disease on the display module 140. In this case, information about the disease may include the name of the disease, major symptoms of the disease, and an explanation of the disease.

Referring to FIG. 2C, the processor 160 may extract four diseases corresponding to the queries selected by the user and generate diagnosis results corresponding to the respective diseases. Further, the processor 160 may display diagnosis results including the names of the extracted diseases and explanations of the diseases on the display module 140 through the self-diagnosis interface.

Further, the processor 160 may further include a "Hospital Search" button that enables the user to search for a hospital corresponding to the diagnosis result and may display the button on the display module 140. If the user clicks the "Hospital Search" button, the processor 160 may show a list of hospitals corresponding to the diagnosis result or may show a list of hospitals or locations thereof by using a map interface including a map image.

Specifically, if the user clicks the "Hospital Search" button through the input module 130, the processor 160 may filter hospitals matched to a disease included in the diagnosis result. Further, if there are multiple kinds of hospitals corresponding to the disease, the processor 160 may display a list to select the kind of hospital that enables the user to select one of the multiple kinds of hospitals.

In this case, the kind of hospital may correspond to a specialty subject, such as ophthalmology, orthopedics, and rehabilitation medicine, corresponding to the disease. Otherwise, the kind of hospital may correspond to a clinic corresponding to the disease, but may not be limited thereto.

Figure 3:
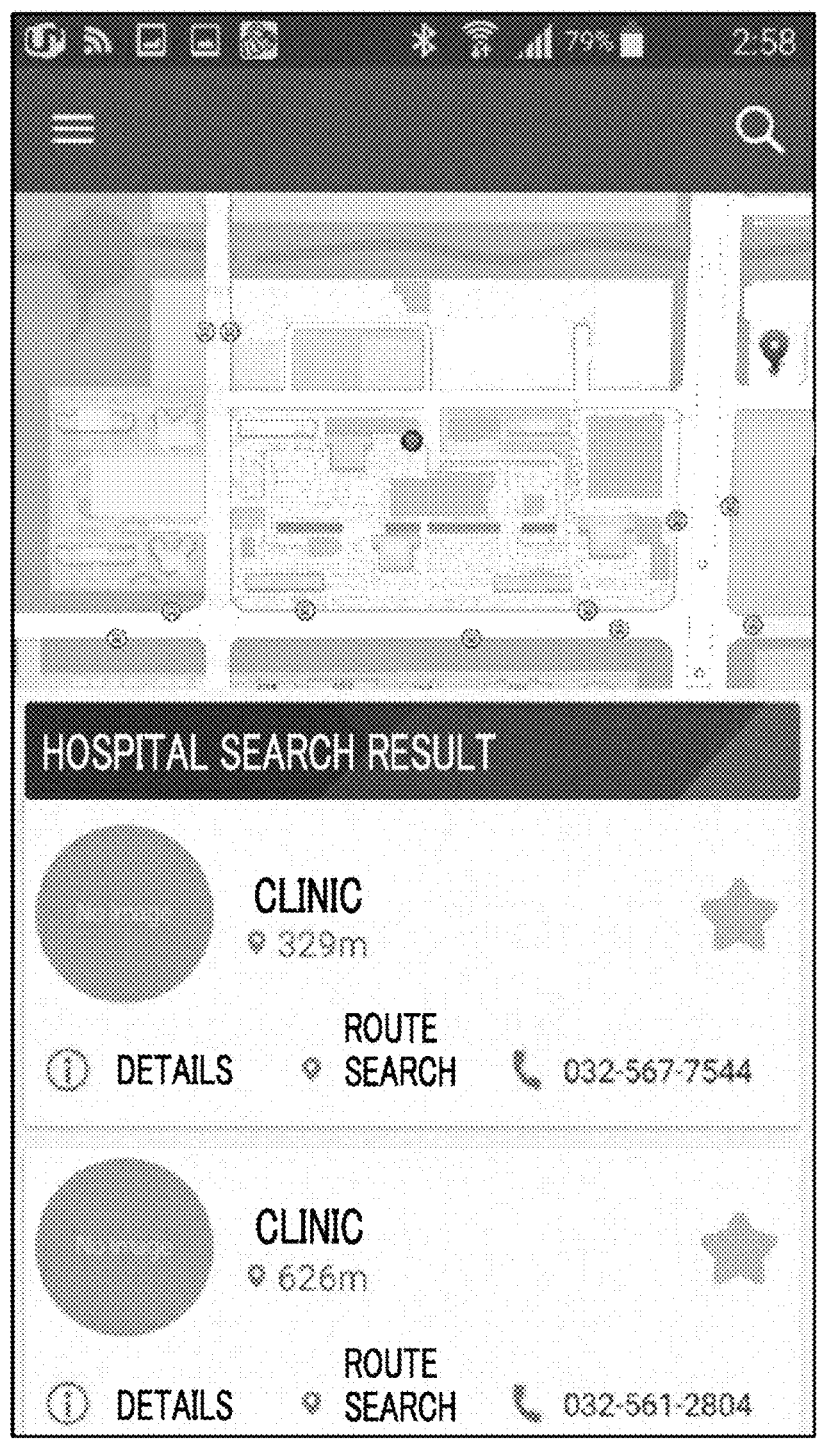
FIG. 3 is an exemplary diagram illustrating a hospital search according to an exemplary embodiment of the present disclosure.

FIG. 3 is an exemplary diagram illustrating a hospital search according to an exemplary embodiment of the present disclosure.

For example, the processor 160 may extract location information of the diagnostic apparatus 100. For example, the processor 160 may extract location information of the diagnostic apparatus 100 through the GPS sensor module 120. Otherwise, the processor 160 may extract location information of the diagnostic apparatus 100 on the basis of the communication module 110.

The processor 160 may merge the location information of the diagnostic apparatus 100 with the map interface. In this case, the map interface may be a prestored map image or may be provided through a map service API. Thus, the location of a hospital may be provided through the map interface.

The processor 160 may display one or more hospitals and information about the hospitals on a map image through the display module 140 on the basis of the location information. In this case, the information about the hospitals may include the names, telephone numbers and office hours of the hospitals. Further, the information about the hospitals may include distance information from the current location of the diagnostic apparatus, but may not be limited thereto.

When the user selects a hospital, the processor 160 may display information about the selected hospital. Further, if the user asks for guidance to the hospital, the processor 160 may provide information about a route to the selected hospital from the current location on the basis of the map service API.

In this case, the processor 160 may extract hospitals matched to the diagnosis result on the basis of the location information and the order of priority. The processor 160 may display a list of the extracted hospitals together with the map interface.

In this case, the order of priority may be set by giving a higher priority to a hospital in order of proximity to the diagnostic apparatus 100 on the basis of the location information. Further, the order of priority may be set by giving a higher priority to a hospital in office hours on the basis of the current time information. Otherwise, the order of priority may be set and transferred by the medical information providing server 410. For example, even if there is a hospital A closest in distance among searched multiple hospitals, in the case where a hospital B is an advertiser who pays an advertisement cost to a manager of the server 410, the hospital B may be provided by priority. Further, information only about the hospital B may be set to include specific PR information of the hospital such as a profile photo, career records of a hospital director, and service guide information.

Meanwhile, if the user visits a hospital matched to a diagnosis result or makes an appointment with a doctor of the hospital, the processor 160 may provide the diagnosis result to the medical information providing server 410 through the communication module 110 in order for a medical team of the hospital to use the diagnosis result as preliminary medical examination information.

For example, the user may select any one of filtered hospitals corresponding to a diagnosis result and make a request for a reservation. In response to the user's reservation request, the processor 160 may transfer a reservation request message for the selected hospital to the medical information providing server 410 through the communication module 110. Further, the processor 160 may receive a reservation confirmation message of the hospital from the medical information providing server 410 and display the reservation confirmation message through the display module 140.

Furthermore, the processor 160 may provide the diagnosis result to the hospital (a device of the hospital or a device of a doctor working at the hospital) for which a reservation is made, through the medical information providing server 410. Then, the processor 160 may provide the diagnosis result and medical records of the user corresponding to the diagnosis result to the hospital for which a reservation is made, through the medical information providing server 410. In this case, the diagnosis result and the medical records may be used as preliminary medical examination information about the user.

For example, the medical records may include information about a disease for which the user was treated or is being treated. Further, the medical records may include the results of past medical examinations of the user. Otherwise, the medical records may include medical certificates or prescriptions corresponding to the user. Further, the medical records may include demographic information about the user, but may not be limited thereto.

In general, a patient with a specific chronic disease wants to be treated in only one hospital. This is because the patient's overall medical history can be stored in the one hospital, and, thus, the hospital can offer a personalized treatment to the patient. However, in the case where the server is configured to transmit medical records as described above, an application executed by the server can function just like a family doctor.

Further, the processor 160 may store the medical records of the user in the memory 150 or transfer the medical records to the medical information providing server 410 and then store the medical records in the medical information providing server 410. In this case, the medical records may be uploaded by the user or generated on the basis of images taken by a camera module (not illustrated). For example, the medical records may be an image of a prescription and may be a text converted from an image through an optical character recognition (OCR) module.

Further, if the user receives a medical treatment from the hospital, the processor 160 may transfer a medical record issued by the hospital to the medical information providing server 410.

Otherwise, the processor 160 may request the hospital to upload a medical record. In response to the request, a medical team device 440 of the hospital may transfer the medical record of the user to the medical information providing server 410. Then, if the medical team device 440 transfers the medical record of the user to the medical information providing server 410, the processor 160 may receive the medical record through the communication module 110.

Meanwhile, the processor 160 may display a disease information user interface on the display module 140 in order to enable the user to search for disease information.

In this case, the disease information may include the name of a disease, symptoms of the disease, and images corresponding to the disease. Further, the disease information may include information about hospitals related to the disease.

For example, the disease information user interface may include an input window in order to enable the user to directly input information about the disease through the input module 130. Otherwise, the disease information user interface may provide the user with a list including images and the name of the disease and thus enable the user to select.

Meanwhile, as an additional exemplary embodiment, the server 410 may provide feedback on the basis of users' self-diagnosis input results and hospital selection results. For example, disease information has been provided in order from first, second, third, fourth, and fifth places according to the sum of weightings, but if disease information in second place is most selected by a specific number of users or more, a weighting to be given to the disease information in second place may be increased with respect to answers to respective queries. Otherwise, if a specialty subject of a hospital finally selected by users for a specific disease is not identical to a specialty subject to be suggested after the selection of a disease, weightings for respective answers related to the specialty subject may be increased in order to show the specialty subject after the selection of a disease or the specialty subject may appear all the time in association with the disease. Otherwise, if there is a hospital which is most selected by users for a specific disease and the number of users who select the hospital is greater than a predetermined number, a specialty subject of the hospital may appear as the uppermost specialty subject after the selection of a disease or may appear as specially highlighted.

Hereinafter, a medical information providing system 400 and the medical information providing server 410 according to an exemplary embodiment of the present disclosure will be described with reference to FIG. 4 and FIG. 5.

Figure 4:
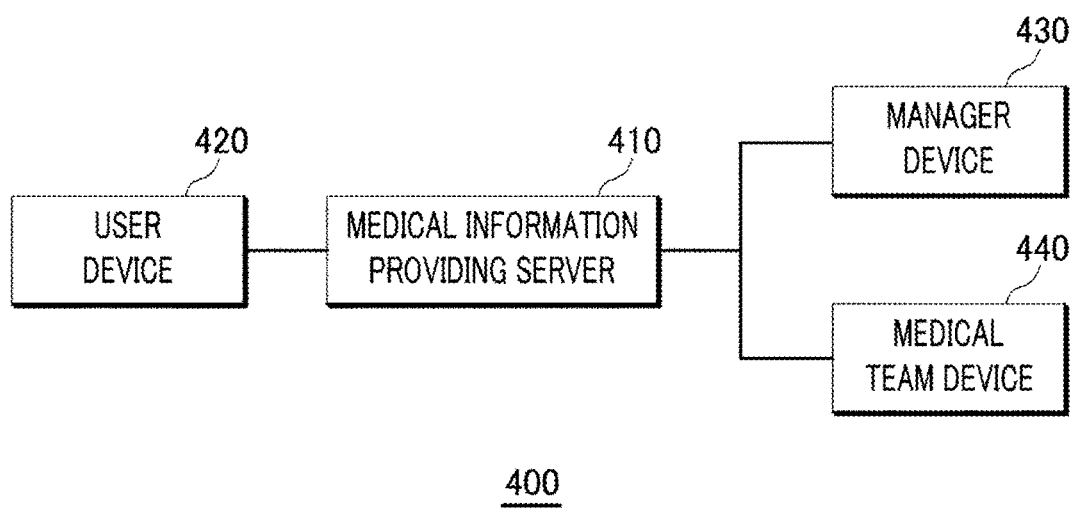
FIG. 4 is a block diagram illustrating a medical information providing system according to an exemplary embodiment of the present disclosure.

FIG. 4 is a block diagram illustrating the medical information providing system 400 according to an exemplary embodiment of the present disclosure.

The medical information providing system 400 includes a user device 420, the medical information providing server 410, a manager device 430, and the medical team device 440.

The user device 420 refers to a device configured to receive medical records or a diagnosis result through the medical information providing server 410. In this case, the user device 420 may be the diagnostic apparatus 100 described above with reference to FIG. 1 to FIG. 3.

Further, the medical team device 440 may refer to a device corresponding to a medical team such as a doctor or a hospital.

Furthermore, the manager device 430 may refer to a device for a user who manages the medical information providing system 400.

The medical information providing server 410 may provide multiple user devices 420 with medical information and queries. The medical information providing server 410 may provide the multiple user devices 420 with information about hospitals corresponding to a diagnosis result.

Further, the medical information providing server 410 may transfer a diagnosis result received from the user device 420 to the medical team device 440 of the corresponding hospital.

Figure 5:
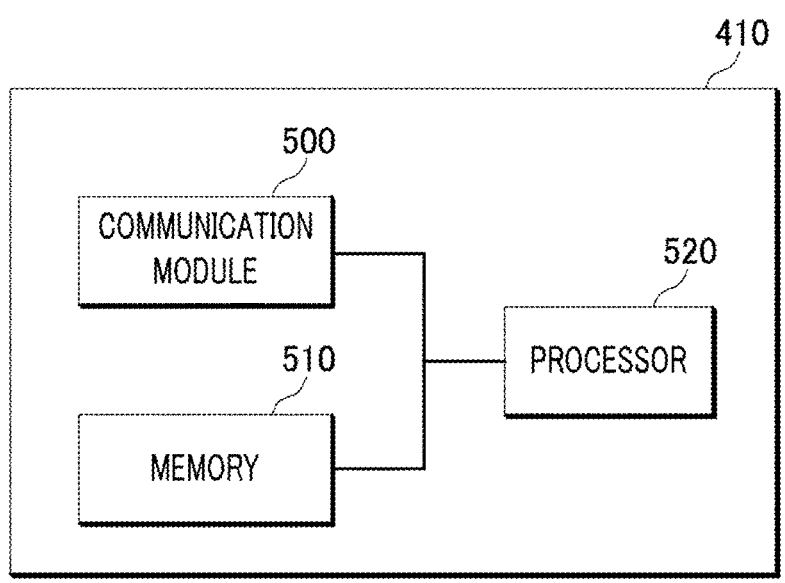
FIG. 5 is a block diagram illustrating a medical information providing server according to an exemplary embodiment of the present disclosure.

FIG. 5 is a block diagram illustrating the medical information providing server 410 according to an exemplary embodiment of the present disclosure.

Herein, the medical information providing server 410 includes a communication module 500, a memory 510, and a processor 520.

The communication module 500 may perform data communication with the user device 420, the manager device 430, and the medical team device 440.

The memory 510 stores a self-diagnosis application therein. Herein, the memory 510 may collectively refer to a non-volatile storage device that retains information stored therein even when power is not supplied and a volatile storage device that requires power to retain information stored therein.

The processor 520 receives a diagnosis result from the user device 420 through the communication module 500. Then, the processor 520 transfers the received diagnosis result to the medical team device 440. In this case, the diagnosis result may be generated on the basis of queries stored in the user device 420. Further, the diagnosis result may be received from the user device 420 after the processor 520 receives a query request message from the user device 420 and transfers a query corresponding to the query request message through the communication module 500.

The query may correspond to a disease. Further, the query may include a predefined weighting corresponding to each disease as described above with reference to Table 1.

For example, the query may be collected through the medical team device 440. Further, the query may be collected by the medical team and uploaded through the manager device 430.

Further, the weighting may be set by the medical team or manager who has the authority to upload a query or modify a query. Otherwise, the weighting may be automatically set on the basis of an answer from the user device 420, but may not be limited thereto.

For example, the weighting may be set or modified by analyzing the query or feedback of the medical team device 440 for a disease including the query. Further, the weighting may be set or modified on the basis of the number of times of feedback.

In the case where the user device 420 makes a request for a query, the processor 520 may transfer all queries to the user device 420 or may transfer a query corresponding to a body part selected by the user device 420 to the user device 420.

Then, the processor 520 may receive a diagnosis result from the user device 420 through the communication module 500. In this case, the processor 520 may generate the diagnosis result after the user's answer to the query is received and then transfer the diagnosis result again to the user device 420. Otherwise, the user device 420 may generate the diagnosis result by analyzing the user's answer to the query and then transfer the diagnosis result.

The processor 520 may transfer the diagnosis result received from the user device 420 to the medical team device 440.

In this case, the medical team device 440 may correspond to a hospital for which the user corresponding to the user device 420 makes a reservation or to which the user agrees to provide information. Otherwise, the medical team device 440 may be a hospital included in medical records corresponding to the user device 420.

Meanwhile, the processor 520 may generate a list of multiple hospitals and transfer the list to the user device 420. In this case, the list of hospitals may include information about the hospitals. For example, the information about the hospitals may include location information of the hospitals, the order of priority among the hospitals, and information about medical teams of the hospitals.

In this case, the order of priority among the hospitals may be set on the basis of advertisement. For example, if a specific hospital requests an advertisement or pays an advertisement cost, the processor 520 may set the hospital to have a higher priority than the other hospitals. In this case, the order of priority may be automatically set on the basis of advertisement cost or manually set by the manager device 430.

Further, the order of priority may be set in order of the number of reviews input through user devices 420, the number of positive reviews, the number of recommendations, and the number of users who make an addition to reservations or bookmarks, but may not be limited thereto.

Meanwhile, the processor 520 may generate information about a hospital to include career records of a medical team working at the hospital. For example, if a specific hospital requests an advertisement, the processor 520 may generate information about the hospital to include career records or images of a medical team of the hospital.

Hereinafter, a method of providing a self-diagnosis result to be performed by the diagnostic apparatus 100 according to an exemplary embodiment of the present disclosure will be described with reference to FIG. 6.

Figure 6:
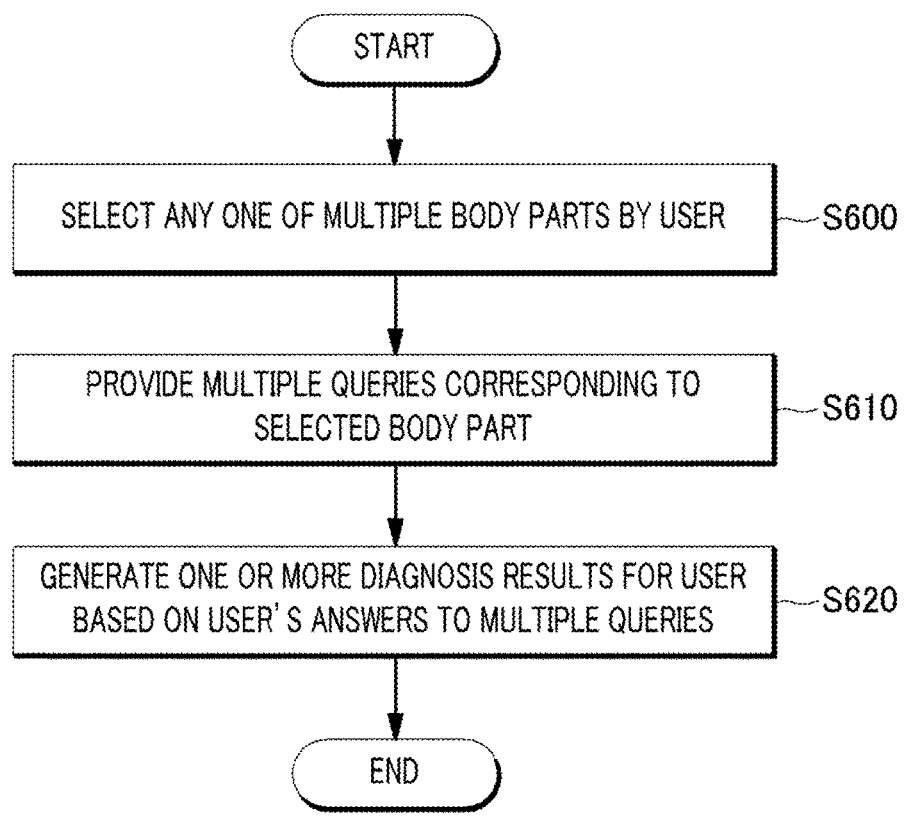
FIG. 6 is a flowchart showing a method of providing a self-diagnosis result to be performed by a diagnostic apparatus according to an exemplary embodiment of the present disclosure.

FIG. 6 is a flowchart showing the method of providing a self-diagnosis result to be performed by the diagnostic apparatus 100 according to an exemplary embodiment of the present disclosure.

The diagnostic apparatus 100 receives the user's input signal to select any one of multiple body parts (S600).

Further, the diagnostic apparatus 100 extracts multiple queries corresponding to the selected body part (S610). In this case, the queries correspond to at least one of multiple diseases.

The diagnostic apparatus 100 generates a diagnosis result for the user on the basis of the user's answers to the multiple queries (S620).

The diagnostic apparatus 100, the medical information providing server 410, and the method of providing a self-diagnosis result of the diagnostic apparatus 100 can generate a diagnosis result including a user's disease by analyzing the user's answers to queries and provide the diagnosis result to the user.

Therefore, the diagnostic apparatus 100, the medical information providing server 410, and the method of providing a self-diagnosis result of the diagnostic apparatus 100 enable the user to select a hospital on the basis of the diagnosis result matched to his/her symptom and take medical treatment.

The diagnostic apparatus 100, the medical information providing server 410, and the method of providing a self-diagnosis result of the diagnostic apparatus 100 can provide a medical team with a diagnosis result as preliminary medical examination information. Further, the diagnostic apparatus 100, the medical information providing server 410, and the method of providing a self-diagnosis result of the diagnostic apparatus 100 can provide the medical team with data including the user's diagnosis result and past medical records. Therefore, the diagnostic apparatus 100, the medical information providing server 410, and the method of providing a self-diagnosis result of the diagnostic apparatus 100 can support the medical team to make a diagnosis with high accuracy and high efficiency on the basis of the data.

An exemplary embodiment of the present disclosure can be embodied in a storage medium including instruction codes executable by a computer such as a program module executed by the computer. Besides, the data structure in accordance with the embodiment of the present disclosure can be stored in the storage medium executable by the computer. A computer-readable medium can be any usable medium which can be accessed by the computer and includes all volatile/non-volatile and removable/non-removable media. Further, the computer-readable medium may include all computer storage and communication media. The computer storage medium includes all volatile/non-volatile and removable/non-removable media embodied by a certain method or technology for storing information such as computer-readable instruction code, a data structure, a program module or other data.

The system and method of the present disclosure has been explained in relation to a specific embodiment, but its components or a part or all of its operations can be embodied by using a computer system having general-purpose hardware architecture or desirably, a digital signal processing system to which an order of priority can be applied.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

I claim:

1. A diagnostic apparatus that provides a self-diagnosis result, comprising:
a touch screen panel configured to receive an input from a user;
a global positioning system sensor configured to detect a location of the diagnostic apparatus;
a camera module configured to capture an image;
a display module configured to display a self-diagnosis user interface including images corresponding to multiple body parts;
a memory in which a self-diagnostic application is stored; and
a processor configured to, upon execution of the self-diagnostic application:
receive an image of a prescription captured by the camera module;
obtain a text converted from the image of the prescription through an optical character recognition (OCR) module;
add the text to medical records for the user stored in the memory;
receive a signal related a selection of a body part among the multiple body parts from the display module;
instruct the display module to display multiple queries corresponding to the body part on the self-diagnosis user interface, each of the queries including predefined weightings corresponding to respective disease;
calculate scores for multiple diseases corresponding to the selected body part on the basis of the user's answers to the respective queries and the predefined weightings corresponding to the respective queries, wherein if a symptom included in the user's answers is the same as that of various diseases, each disease is given a different weighting depending on whether the symptom is a major symptom of the disease;
select one or more diseases from among the multiple diseases on the basis of the scores for the multiple diseases;
instruct the display module to display a diagnosis result including the one or more diseases in order of the scores for the one or more diseases on the self-diagnosis user interface;
receive a selection of a disease among the one or more diseases;
instruct the display module to display, on a prestored map image provided through a map service API, a list of hospitals corresponding to the selected disease and a distance to each of the hospitals based on the location of the diagnostic apparatus;
receive a selection of a hospital by the touch screen panel; and
transmit the diagnosis result and the medical records for the user to a device of the selected hospital in response to the selection of the hospital,
wherein the predefined weightings are adjusted in response to determining that the score for the selected disease is not highest among scores for the one or more diseases; and
the predefined weightings are adjusted in response to determining that a specialty subject of the selected hospital for the selected disease is not identical to a specialty subject provided in response to the selection of the disease;
wherein the processor instructs the display module to display a predetermined number of queries on the self-diagnosis user interface;
determines whether a score for a first disease among the multiple diseases after receiving the user's answers to the predetermined number of queries is greater by a predetermined score than each of scores of any other diseases of the multiple diseases;
selects queries corresponding to first disease in response to determination that the score for the first disease among the multiple diseases after receiving the user's answers to a predetermined number of queries is greater at least by the predetermined score than each of scores of any other diseases of the multiple diseases; and
instruct the display module to display the selected queries on the self-diagnosis user interface after displaying the predetermined number of queries; and
wherein the medical records include at least one of results of past medical examination, medical certificates, prescriptions, and demographic information.

2. The diagnostic apparatus of claim 1, further comprising:
a communication module configured to perform data communication with a server,
wherein the processor extracts a hospital corresponding to the selected disease on the basis of an order of priority received from the server and the location information.

3. The diagnostic apparatus of claim 2,
wherein the processor transfers a medical record corresponding to the diagnosis result to the server.

4. The diagnostic apparatus of claim 1,
wherein the processor displays a disease information user interface including information about multiple diseases on the self-diagnosis user interface, and the information about the diseases include names of the diseases, symptoms of the diseases, and images corresponding to the diseases.

5. A system for providing a self-diagnosis result, the system comprising:
the diagnostic apparatus of claim 1; and
a medical information providing server, comprising:
a communication module;
a memory in which a diagnosis result providing program is stored; and
a processor configured to execute the program,
wherein upon execution of the program, the processor transfers a diagnosis result received from the diagnostic apparatus to a medical team device.

6. The system of claim 5,
wherein the processor receives feedback corresponding to a disease from one or more medical team devices, and updates a query corresponding to the disease and a predefined weighting included in the query corresponding to the disease on the basis of the feedback corresponding to the disease and transfers the updated query and weighting to the diagnostic apparatus.

7. The system of claim 5,
wherein the processor of the medical information providing server generates information about one or more hospitals and transfers the generated information to the diagnostic apparatus, and
the information about the hospitals includes location information of the hospitals and an order of priority corresponding to the hospitals.

8. A method of providing a self-diagnosis result for a user to be performed by a diagnostic apparatus, comprising:
capturing an image of a prescription by a camera module;
obtaining a text converted from the image of the prescription through an optical character recognition (OCR) module;
adding the text to medical records for the user stored in the memory;
displaying, on a self-diagnosis user interface of a diagnostic apparatus, images corresponding to multiple body parts;
receiving, by a touch screen panel of the diagnostic apparatus, a signal related a selection of a body part among the multiple body parts;
displaying, on the self-diagnosis user interface of the diagnostic apparatus, multiple queries corresponding to the body part, each of the queries including predefined weightings corresponding to respective disease;
calculating scores for multiple diseases corresponding to the selected body part
on the basis of the user's answers to the respective queries and the predefined weightings corresponding to the respective queries, wherein if a symptom included in the user's answers is the same as that of various diseases, each disease is given a different weighting depending on whether the symptom is a major symptom of the disease;
selecting one or more diseases from among the multiple diseases on the basis of the scores for the multiple diseases;
displaying, on the self-diagnosis user interface of the diagnostic apparatus, a diagnosis result including the one or more diseases in order of the scores for the one or more diseases;
receiving a selection of a disease among the one or more diseases;
detecting, using a global positioning system sensor, a location of the diagnostic apparatus;
displaying, on a map image provided through a map service API and stored in the diagnostic apparatus, a list of hospitals corresponding to the selected disease and a distance to each of the hospitals based on the location of the diagnostic apparatus;
receiving, by the touch screen panel of the diagnostic apparatus, a selection of a hospital;
transmitting the diagnosis result and the medical records for the user to a device of the selected hospital in response to the selection of the hospital;
adjusting the predefined weightings in response to determining that the score for the selected disease is not highest among scores for the one or more diseases; and
adjusting the predefined weightings in response to determining that a specialty subject of the selected hospital for the selected disease is not identical to a specialty subject provided in response to the selection of the disease,
wherein displaying, on the self-diagnosis user interface of the diagnostic apparatus, multiple queries corresponding to the body part, each of the queries including predefined weightings corresponding to respective disease comprises:
displaying a predetermined number of queries on the self-diagnosis user interface of the diagnostic apparatus;
determining whether a score for a first disease among the multiple diseases after receiving the user's answers to the predetermined number of queries is greater by a predetermined score than each of scores of any other diseases of the multiple diseases;
selecting queries corresponding to first disease in response to determination that the score for the first disease among the multiple diseases after receiving the user's answers to the predetermined number of queries is greater at least by the predetermined score than each of scores of any other diseases of the multiple diseases; and
displaying, on the self-diagnosis user interface of the diagnostic apparatus, the selected queries after displaying the predetermined number of queries; and
wherein the medical records include at least one of results of past medical examination, medical certificates, prescriptions, and demographic information.

* * * * *